United States Patent [19]
Leroy et al.

[11] Patent Number: 5,037,415
[45] Date of Patent: Aug. 6, 1991

[54] DIAPER WITH ELASTICIZED CROTCH

[75] Inventors: Andre Leroy, Mouvaux; Bernard Deleu, Linselles, both of France; Alain Naze, Bas-Warneton, Belgium

[73] Assignee: Peaudouce, Linselles, France

[21] Appl. No.: 443,171

[22] Filed: Nov. 30, 1989

[30] Foreign Application Priority Data

Nov. 30, 1988 [FR] France ................................ 88 15715

[51] Int. Cl.⁵ .............................................. A61F 13/15
[52] U.S. Cl. .............................. 604/385.1; 604/385.2; 604/396
[58] Field of Search ................. 604/385.1, 385.2, 386, 604/387; 156/161, 164

[56] References Cited

U.S. PATENT DOCUMENTS

| | | | |
|---|---|---|---|
| 3,860,003 | 1/1975 | Buell | 604/385.2 |
| 4,081,301 | 3/1978 | Buell | 156/164 |
| 4,353,762 | 10/1982 | Bouda | 156/164 |
| 4,408,397 | 9/1983 | Teed | 156/164 |
| 4,450,026 | 5/1984 | Pieniak et al. | 156/164 |
| 4,525,229 | 6/1985 | Suzaki et al. | 156/161 |
| 4,661,102 | 4/1987 | Shikata et al. | 604/385.2 |
| 4,666,542 | 5/1987 | De Sondechese | 156/164 |
| 4,850,989 | 7/1989 | Villez | 604/385.2 |
| 4,917,695 | 4/1990 | Villez | 604/385.2 |

FOREIGN PATENT DOCUMENTS

2583620 12/1986 France ................................ 604/385.1

Primary Examiner—Randall L. Green
Assistant Examiner—K. Reichle
Attorney, Agent, or Firm—Owen, Wickersham, & Erickson

[57] ABSTRACT

Diaper for disposal after use, comprising an outer sheet (1) which is impermeable to liquids, an inner sheet (2) which is permeable to liquids, an absorbent pad (3), elastic elements (18) extending in the extended state along the opposite longitudinal edges of the absorbent pad, and fastener elements (11) for closing the diaper around the waist of the user.

The diaper also comprises two longitudinal strips (14) extending in the stretched state over the entire length of the diaper along the opposite longitudinal edges of the pad (3), between the two sheets (1, 2), each of the strips being fastened at least along its outer longitudinal edge (15) and along its two transverse edges to the outer sheet (1) and along its two opposite longitudinal edges (16) and along its two transverse edges to the inner sheet (2), and the elastic elements (18) are fastened in the extended state on the strips (14) between the two opposite longitudinal edges (15, 16) of the latter.

13 Claims, 4 Drawing Sheets

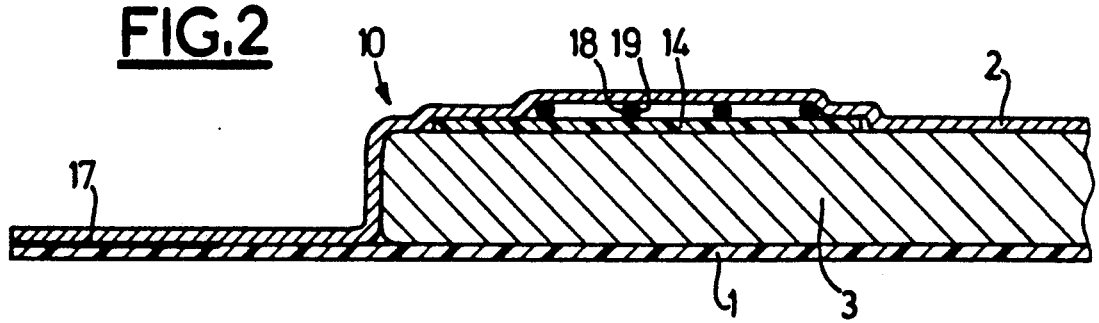
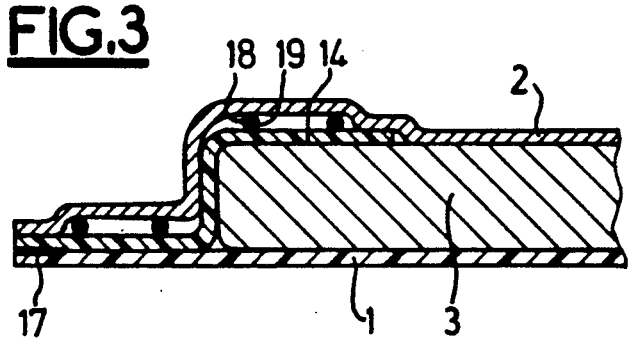
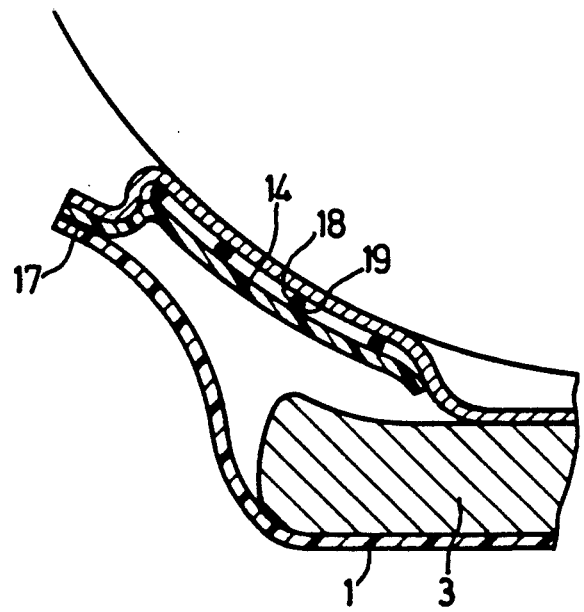

DIAPER WITH ELASTICIZED CROTCH

The present invention relates to nappy pants or diapers for disposal after use, or to a similar hygiene article, which may be used for children or adults, comprising an absorbent pad, an outer sheet which is impermeable to liquids, an inner sheet which is permeable to liquids, the absorbent pad being disposed between the said two sheets, elastic elements extending in the elastically extended state along the two opposite longitudinal edges of the absorbent pad, and means for closing the nappy pants around the waist of the user.

On known nappy pants or diapers of this type, the longitudinal elastic elements intended to apply the nappy pants against the thighs are generally fastened to the inner face of the outer impermeable sheet, outside the longitudinal edges of the nappy pants. These arrangements present a number of drawbacks.

On the one hand, the role of the elastic elements in applying the nappy pants against the thighs of the user may be disturbed by the absorbent pad disposed therebetween, in particular when the pad is thick and/or rigid, which can lead to a gaping which adversely affects leaktightness in this zone which is particularly susceptible to leakage. Moreover, the nappy pants may have a "swollen" appearance at the location of the absorbent pad, between the elastic elements (an appearance referred to as "boxing glove" appearance). Moreover, when, as is generally the case, the nappy pants are manufactured continuously in the longitudinal direction and the elastic elements are positioned continuously after having been glued at intervals and are then cut in the non-glued spaces such that these non-glued sections contract freely, it is necessary to provide, between the two sheets of the nappy pants, non-glued zones in order to permit this free contraction of the elastic elements, it then being possible for these non-glued zones to give rise to leakage of the material making up the pad and/or of liquid absorbed by the pad. Finally, on nappy pants comprising an absorbent pad in the shape of an hourglass, with lateral recesses in the so-called crotch zone, the longitudinal elastic elements are fastened to the outer impermeable sheet only over the length of these recesses, which, when the nappy pants are put on the user, cause the application against the thighs to be limited to one part only of the circumference of the thighs, which can give rise to leakage in the remaining part.

Attempts have certainly already been made to remedy some of the abovementioned drawbacks. It is known from European Patent Application Nos. 219,326, 243,013 and 251,332 to fasten the longitudinal elastic elements not on the outer impermeable sheet disposed flat, but on lateral "flaps" projecting upwards and having a certain freedom of movement relative to the outer sheet and, consequently, relative to the absorbent pad. However, these arrangements involve considerable complication of the manufacture of the nappy pants, which results in a high cost price which is incompatible with the destination of these products (products of the type for disposal after use).

Moreover, it is known, for example, from European Patent Application No. 0,270,979 to eliminate the risks of leakage via non-glued zones provided between the two sheets of nappy pants with longitudinal elastic elements by providing longitudinal strips covering the elastic elements and fastened to the outer sheet on either side of the elastic elements over the entire length of the nappy pants. However, this does not remedy the other abovementioned drawbacks relating to the elastic elements fastened to the outer sheet.

It is also known from European Patent Application No. 0,149,999, for manufacturing nappy pants, to use an outer sheet with a width that is greater than the width of the nappy pants, to fold this sheet in the form of two lateral leaves on top of the absorbent pad and to fasten longitudinal elastic elements on the said leaves. The leaves, which afford the elastic elements a certain freedom relative to the absorbent pad and also relative to the remaining part (lower fold) of the outer sheet, are fastened at their longitudinal ends to the lower fold of the outer sheet, but are free over the remaining part of their length, which compromises their correct position under the pull of the elastic elements which distort the leaves.

Thus, it appears that the attempts made hitherto in order to remedy the drawbacks of conventional nappy pants with longitudinal elastic elements fastened in the extended state to the outer impermeable sheet are not entirely satisfactory.

The present invention has as its subject nappy pants which better fulfil the requirements imposed on articles of this type. The invention has as its subject nappy pants which, while being of simple structure and manufacture, enable the elastic elements to ensure perfect application against the thighs of the user without this application being disturbed or thwarted by the presence of the absorbent pad between the elastic elements. The invention also has as its subject nappy pants of simple manufacture which eliminate, or, at least, reduce, the risks of leakage due to the presence, between the two sheets, of non-glued zones in order to permit the contraction of the non-glued parts of the longitudinal elastic elements. Moreover, the invention has as its subject nappy pants of the type with an absorbent pad in the form of an hourglass on which the elastic elements may ensure application against the thighs of the user over the entire circumference of the thighs and, in particular, over a length which is greater than the length of the lateral recesses of the absorbent pad.

The nappy pants according to the invention, of the type for disposal after use, comprise an outer sheet which is impermeable to liquids and an inner sheet which is permeable to liquids, the two sheets of extended form having, in practice, the same dimensions and being superposed. The nappy pants further comprise an absorbent pad of extended form having a length and a width which are smaller than those of the said sheets and which pad is disposed between the said sheets such that its edges are set back relative to the edges of the said sheets, the two sheets being joined together around the pad. Moreover, the nappy pants comprise elastic elements extending in the extended state along the opposite longitudinal edges of the absorbent pad. Finally, the nappy pants comprise means for closing the nappy pants around the waist of the user. According to the invention, the nappy pants also comprise two longitudinal strips extending in the stretched state over the entire length of the nappy pants, along the opposite longitudinal edges of the absorbent pad, between the said two sheets, each of the said strips being fastened to the outer sheet at least along the centre part of its outer longitudinal edge and along its two transverse edges and to the inner sheet along its two opposite longitudinal edges and along its two transverse edges. The elastic elements are fastened in the extended state to the said strips, between the two opposite longitudinal edges of the latter.

The elastic elements are preferably fastened in the extended state on the face of the strips facing towards the inner sheet.

Moreover, additional elastic elements may be fastened to the outer sheet which is impermeable to liquids.

The strips may be disposed either outside the opposite longitudinal edges of the absorbent pad, or such that the inner longitudinal edges of the strips are located on the face of the pad which faces towards the inner sheet which is permeable to liquids, the strips thus straddling the opposite longitudinal edges of the pad at least in the centre part of the length of the latter. In this case, the strips preferably consist of a material which is impermeable to liquids.

In the case of nappy pants in the form of an hourglass comprising two sheets in the form of an hourglass which are obtained by cutting out a lateral recess in each of the two opposite longitudinal edges of the sheets, the strips carrying the elastic elements may be disposed relative to the said sheets such that their outer longitudinal edges are located outside the base of the lateral recesses in the sheets, such that the cutting-out of the recesses in the two sheets also involves the cutting-out of recesses in the strips.

In the case of nappy pants with absorbent pads in the form of an hourglass having recesses in their two opposite longitudinal edges, the elastic elements are advantageously fastened in the extended state to the strips over a length which is greater than the length of the recesses in the pad.

Although it is possible within the scope of the invention to fasten only one single elastic element to each strip, it is advantageous to fasten several elastic elements spaced parallel on each strip.

A more detailed description will be given below, with reference to the appended drawings, of an illustrative, non-limiting embodiment of nappy pants according to the invention; in the drawings:

FIGS. 2 and 3 are partial sections, on a larger scale, along II—II and III—III of FIG. 1;

FIG. 4 is a section similar to that in FIG. 3 showing the nappy pants during use;

Figure 1:
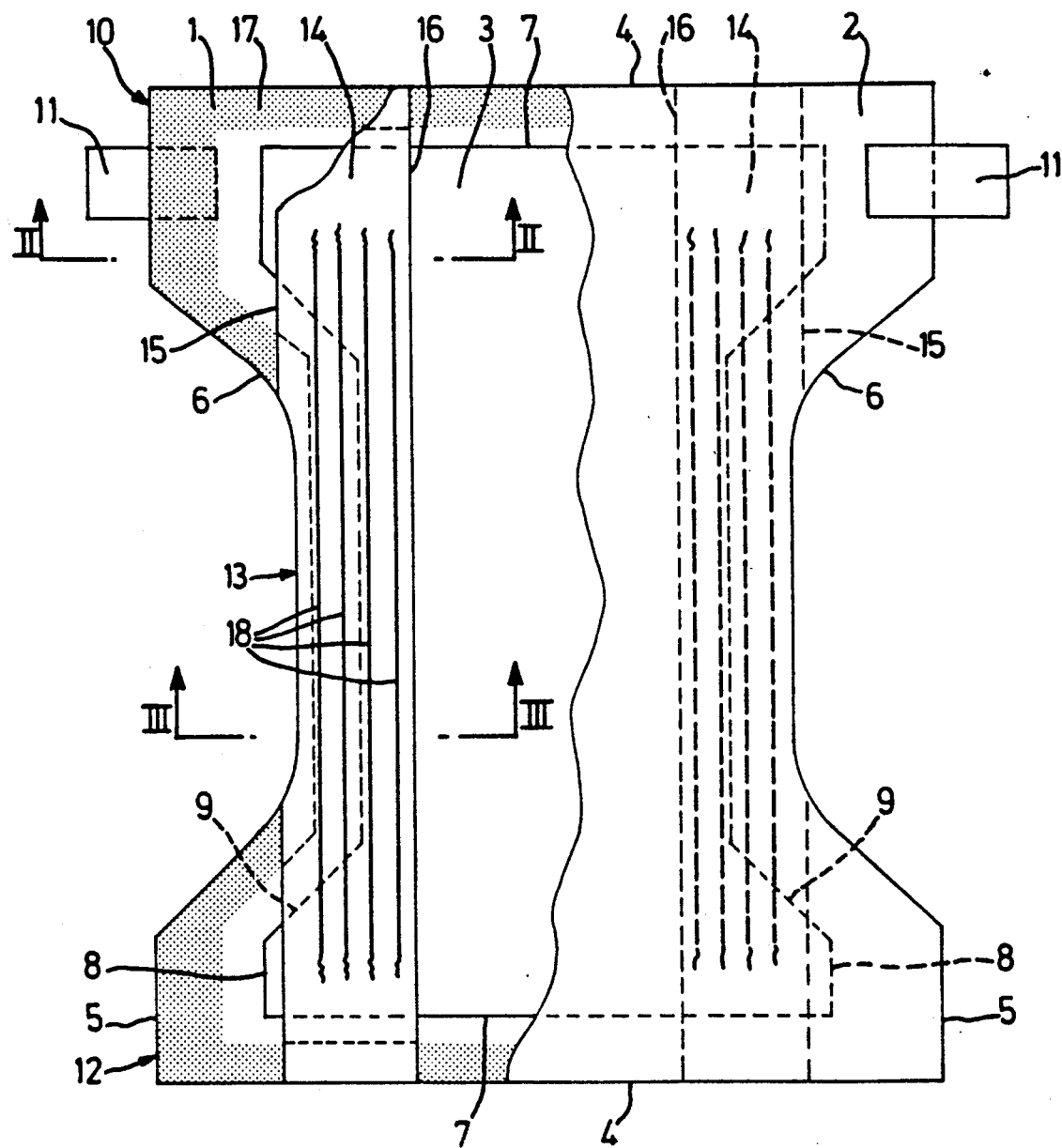
FIG. 1 is a view over the inner face of nappy pants according to the invention disposed flat, with the inner sheet which is permeable to liquids having been partially removed.

The nappy pants for disposal after use, as illustrated by the drawings, comprise an outer sheet 1 which is impermeable to liquids, for example a sheet of polyethylene, an inner sheet 2 which is permeable to liquids, for example a sheet of nonwoven material, and an absorbent pad 3, for example based on defibred cellulose pulp, called "cellulose fluff", incorporating or otherwise particles of superabsorbent material. Absorbent pads of this type are well known and their particular structure, the nature of the materials used, etc. are not covered by the scope of the present invention.

The two sheets 1 and 2 have the same hourglass form, that is to say a generally rectangular form with two opposite transverse edges 4 which are rectilinear and two opposite longitudinal edges 5 which are each equipped with a recess 6 in the centre part of the length thereof.

The absorbent pad 3 also has an hourglass form and is disposed in a central position, relative to the two sheets 1, 2, between the latter, such that its two transverse edges 7 which are rectilinear and its two longitudinal edges 8 which are each equipped with a recess 9 substantially in the centre of its length are set back relative to the edges 4 and 5/6 of the sheets 1, 2.

At least the outer sheet 1 is also equipped, in the wider rear part 10 of the nappy pants, located on one side of the recesses 6, with adhesive-attached elements 11 intended to be fastened, with a view to the closure of the nappy pants around the user, on the wider front part 12 of the nappy pants, the intermediate part 13, called the crotch part, defined by the recesses 6, being located between the thighs of the user.

A strip 14 of a flexible material which is impermeable to liquids, for example of polyethylene sheet, extends between the two sheets 1 and 2 over the entire length of the nappy pants, along each longitudinal edge of the absorbent pad 3, the strips being located between the absorbent pad 3 and the inner sheet 2 which is permeable to liquids. The outer longitudinal edge 15 of each strip 14 is slightly offset inwards relative to the corresponding longitudinal edge 8 of the pad 3 and slightly offset outwards relative to the base of the corresponding recess 6 in the sheets 1 and 2, such that the cutout of the recesses 6 also slightly affects the strips 14. The inner longitudinal edge 16 of each strip 14 is offset inwards relative to the bottom of the corresponding recess 9 in the absorbent pad 3. Consequently, each strip 14 straddles the corresponding longitudinal edge of the absorbent pad 3 over virtually the entire length of the recess 9, that is to say in the crotch zone.

The strips 14 are fastened to the outer sheet 1 at their two ends as well as along their outer longitudinal edges 15 in the zone of the recesses 6, that is to say essentially in their parts which are in contact with the outer sheet 1. This fastening is accomplished by the fact that the outer sheet 1 is equipped, on its face which faces towards the inner sheet 2, in a manner known per se, with a layer of glue 17 around the entire zone covered by the pad 3 with a view to joining the inner sheet 2 to the outer sheet 1 over the circumference of the pad 3.

Several elastic elements 18, namely four elastic elements in the example shown, are fixed in the extended state on each strip 14 in the centre part of the length of the strip on the face of the strip which faces towards the inner sheet 2. In the example shown, two of the elastic elements 18 are located outside and the two others inside the edge of the absorbent pad 3 defined by the base of the corresponding recess 9 in the pad. The length over which the elastic elements 18 are fastened to the strips 14 is greater than the length of the recesses 9 in the pad 3, such that the elastic elements 18 extend not only over the crotch part 13, but extend over the rear part 10 and the front part 12 of the nappy pants.

With a view to their fastening on the strips 14, the elastic elements 18 are, in a manner known per se, coated with glue over a length corresponding to the length for fastening the elastic elements in the extended state. According to FIGS. 2 and 3, the elastic elements 18 receive a coating of glue 19 over their entire circumference, which causes them to adhere both to the strips 14 and to the inner sheet 2. Consequently, the elastic elements 18 form the join between the strips 14 and the inner sheet 2, such that an additional join, for example by means of a line of glue in the vicinity of the inner longitudinal edge 16 of the strips 14, is not absolutely necessary between the strips 14 and the inner sheet 2.

FIG. 4 shows the independence of the elastic elements 18 relative to the absorbent pad 3, by virtue of their fastening which is not on the outer sheet 1 but on the strips 14 joined to the outer sheet 1 only along their outer longitudinal edge 15 (and at their ends). The risks of the nappy pants gaping in the crotch zone through the action of the movements of the user are thus at least significantly reduced.

Figure 5:
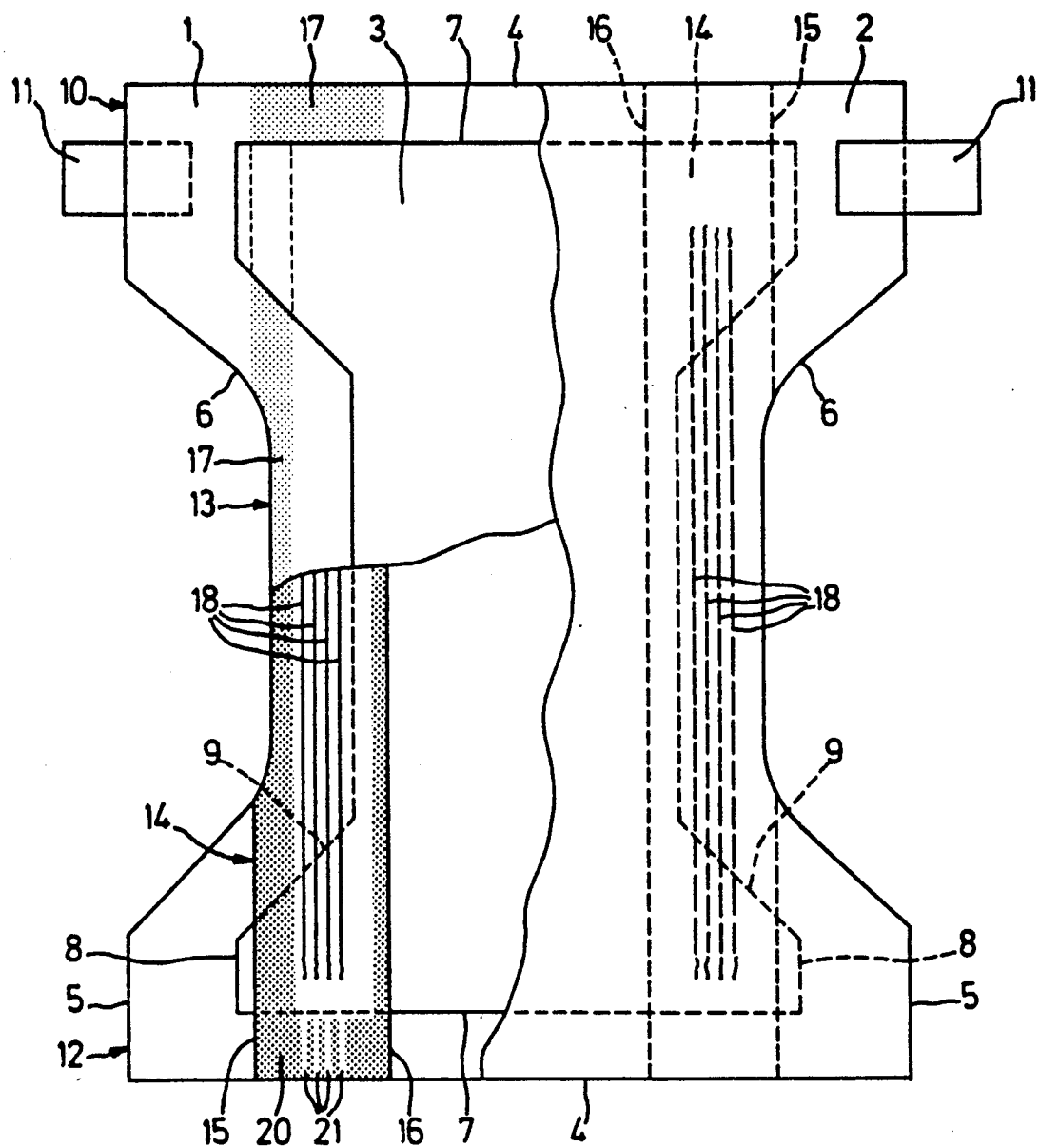
FIGS. 5 and 6 are views similar to FIG. 1 of two other embodiments of the invention.

FIG. 5 shows another embodiment of the invention in which each strip 14 carrying several elastic elements 18 is fastened to the outer sheet 1 by gluing 17 in the form of a U of the latter, this gluing 17 corresponding to the two transverse edges and to the outer longitudinal edge (15) of the strip 14. The strip 14 is, in turn, fastened to the inner sheet 2 by gluing 20, applied either on the strip 14, or preferably on the outer face of the inner sheet 2, so as to extend along the two opposite longitudinal edges 15, 16 and the two transverse edges of the strip 14. It should be noted that, in this case, the elastic elements 18 are not fastened to the inner sheet 2. Moreover, it will be observed, in FIG. 5, that the gluing 20 comprises, at each transverse end of the strip 14, gaps 21 which are located in the extension of the elastic elements 18 and are intended to permit the free contraction of the non-glued sections of the elastic elements during continuous manufacture of the nappy pants.

It should also be noted that, in the embodiment according to FIG. 5, the elastic elements 18, which are 4 in number, are fastened on each strip 14 so as to be located outside the base of each lateral recess 9 in the absorbent pad 3, that is to say outside the longitudinal edge of the pad in the crotch zone 13.

Figure 6:
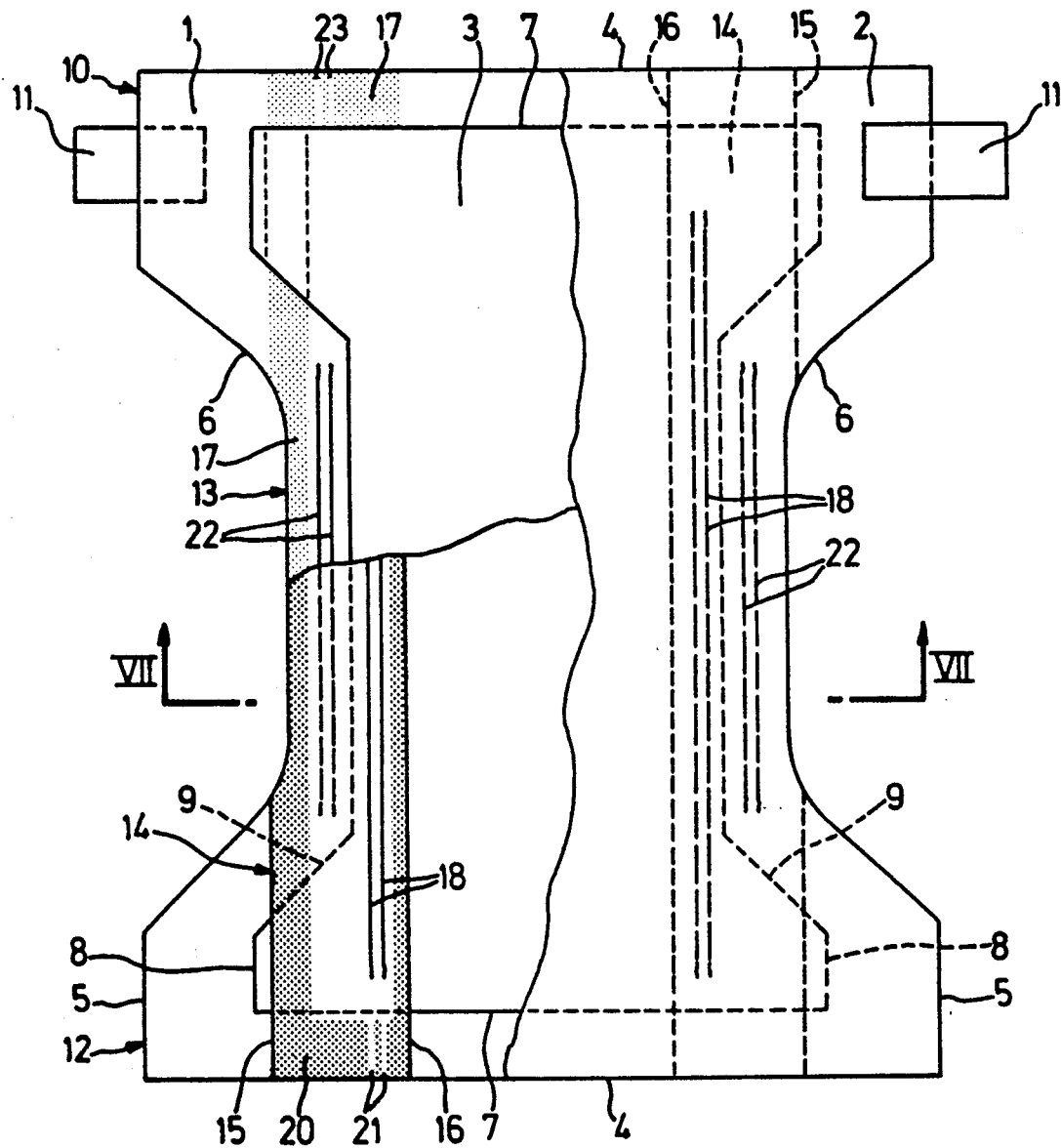
Figure 7:
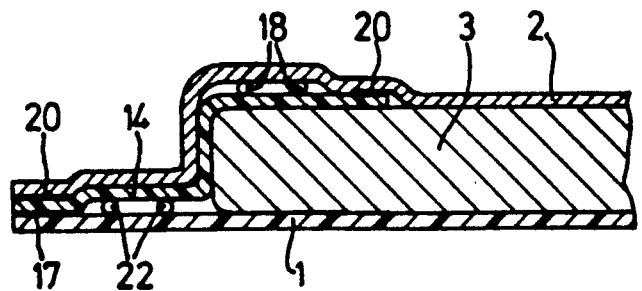
FIG. 7 is a section similar to that in FIG. 3 for the embodiment of FIG. 6.

In the preferred embodiment of the invention illustrated by FIGS. 6 and 7, two longitudinal elastic elements 18 are fastened on each strip 14, on the face which faces towards the inner sheet 2, and two other longitudinal elastic elements 22 are fastened directly on the outer sheet 1, between the base of the recess 9 in the pad 3 and the base of the recess 6 in the sheets 1 and 2. It should be noted that the elastic elements 22 fastened to the outer sheet 1 are shorter than the elastic elements 18 fastened to the strip 14, their length not exceeding the length of the base of the recess 9 in the pad 3 (crotch zone 13). On the other hand, the elastic elements 18 are fastened on the strip 14 over a length which is almost or substantially equal to the length of the absorbent pad 3.

In order to permit the free retraction of the non-glued sections of the elastic elements 22, the U-shaped gluing 17 provided on the outer sheet 1 for fastening each strip 14 to the outer sheet 1 along its two transverse edges and its outer longitudinal edge comprises, in this case, in each of its two transverse parts, two gaps 23 which are aligned with the elastic elements 22.

The two elastic elements 18 fastened by gluing only on the face of each strip 14 which faces towards the inner sheet 2 and not on the inner sheet 2 are disposed on the strip 14 so as to be offset inwards relative to the base of the corresponding recess 9 in the pad 3. In order to permit the free contraction of the non-glued sections of the elastic elements 18, the gluing 20 provided on the strip 14 or on the inner sheet 2 for fastening the strip 14 to the inner sheet 2 along its two opposite longitudinal edges 15, 16 and its two opposite transverse edges comprises, in the transverse parts, gaps 21 located in alignment with the elastic elements 18.

It should be noted that the embodiments represented and described have been given solely by way of illustrative and non-limiting examples and that numerous modifications and variants are possible within the scope of the invention.

Thus, the number of elastic elements 18 fastened on the strips 14 (as well as the number of elastic elements 22 fastened on the outer sheet) may vary between 1 and 4 or even more. The arrangement of the elastic elements relative to the longitudinal edges of the pad (relative to the base of the lateral recesses in the case of pads in the form of an hourglass) is also variable, it being possible for the elastic elements to be disposed outside, inside or straddling the said edges.

The width of the strips 14 is also variable.

Further, it is possible to arrange the strips 14 carrying the elastic elements 18, not straddling the longitudinal edges of the pad 3, but completely outside the pad, at least in the crotch zone 13.

Moreover, it is possible to provide strips 14 having such a width that their outer longitudinal edge 15 is offset outwards with respect to the longitudinal edge 8 of the absorbent pad 3, over the entire length of the latter In that case, the strips 14 are preferably fastened over their entire length to the outer sheet 1 (gluing 17) near their outer longitudinal edge, thus improving the liquid-barrier action of strips 14. That arrangement applies especially to absorbent pads having shallow lateral recesses, or to rectangular pads without lateral recesses.

What is important, within the scope of the invention, is that the elastic elements 18 enjoy an optimum independence relative to the outer sheet 1 and relative to the absorbent pad 3 fastened on the outer sheet 1, so as always to remain applied against the thighs and thus always to ensure an effective barrier, in particular for the retention of faecal matter.

Moreover, the invention may, of course, also be applied to nappy pants and to similar hygiene articles for children and for incontinent adults, said articles and nappy pants not having the shape of an hourglass and/or comprising absorbent pads which are not in the shape of an hourglass.

We claim:

1. Disposable diaper of the type comprising an outer sheet impermeable to liquids, an inner sheet permeable to liquids, said two sheets of elongated form having substantially the same dimensions and being superposed, an absorbent pad of elongated form having a length and a width which are smaller than those of said sheets, which pad is disposed between said sheets such that its edges are set back relative to the edges of said sheets, said two sheets being joined together around the pad, means for closing the diaper around the waist of the user, two longitudinal strips extending over the entire length of the diaper, along the opposite longitudinal edges of said absorbent pad, between said two sheets, each of said strips being fastened to said outer sheet at least along the middle part of its outer longitudinal edge and along its two transverse edges and to said inner sheet along its two opposite longitudinal edges and along its two transverse edges, and longitudinal elastic elements fastened in the stretched state to said strips, between the two opposite longitudinal edges of the latter.

2. Diaper according to claim 1, wherein said elastic elements are fastened on the face of said strips facing towards said inner sheet.

3. Diaper according to claim 2 wherein additional longitudinal elastic elements are fastened in the stretched state to said outer sheet.

4. Diaper according to claim 3, wherein said strips are fastened to said outer sheet by glue zones comprising gaps in alignment with said additional elastic elements.

5. Diaper according to claim 3, wherein said strips are disposed relative to the opposite longitudinal edges of said absorbent pad such that the inner longitudinal edges of said strips are located on the face of said pad which faces towards said inner sheet, said strips thus straddling said opposite longitudinal edges of said pad at least in the middle part of the length of the latter.

6. Diaper according to claim 1, wherein said strips are disposed relative to the opposite longitudinal edges of said absorbent pad such that the inner longitudinal edges of said strips are located on the face of said pad which faces towards said inner sheet, said strips thus straddling said opposite longitudinal edges of said pad at least in the middle part of the length of the latter.

7. Diaper according to claim 1, wherein said strips consist of a material impermeable to liquids.

8. Diaper according to claim 7, in the form of an hourglass, wherein said two sheets in the form of an hourglass comprise a lateral recess in each of their two opposite longitudinal edges, said strips being disposed relative to said sheets such that their outer longitudinal edges are located outside the bottom of said lateral recesses in said sheets, and comprising in their outer longitudinal edges lateral recesses in coincidence with said lateral recesses in said sheets.

9. Diaper according to claim 8, wherein said absorbent pad in the form of an hourglass has recesses in its two opposite longitudinal edges, said elastic elements being fastened in the stretched state of said strips over a length which is greater than the length of said recesses in the pad.

10. Diaper according to claim 9 wherein said strips are fastened to said inner sheet by glue zones comprising gaps in alignment with the elastic elements fastened on the strips.

11. Diaper according to claim 1, in the form of an hourglass, wherein said two sheets in the form of an hourglass comprise a lateral recess in each of their two opposite longitudinal edges, said strips being disposed relative to said sheets such that their outer longitudinal edges are located outside the bottom of said lateral recesses in said sheets, and comprising in their outer longitudinal edges lateral recesses in coincidence with said lateral recesses in said sheets.

12. Diaper according to claim 11, wherein said absorbent pad in the form of an hourglass has recesses in its two opposite longitudinal edges, said elastic elements being fastened in the stretched state to said strips over a length which is greater than the length of said recesses in the pad.

13. Diaper according to claim 1 wherein said strips are fastened to said inner sheet by glue zones comprising gaps in alignment with the elastic elements fastened on the strips.

* * * * *